United States Patent [19]
Dance et al.

[11] Patent Number: 5,601,566
[45] Date of Patent: Feb. 11, 1997

[54] METHOD AND APPARATUS FOR THE ALIGNMENT OF A FEMORAL KNEE PROSTHESIS

[75] Inventors: Mark N. Dance, Ladner; Mark Ward, Surrey, both of Canada; David T. Pollock, Glen Rock, N.J.

[73] Assignee: Osteonics Corp., Allenbale, N.J.

[21] Appl. No.: 199,069

[22] Filed: Feb. 22, 1994

[51] Int. Cl.$^6$ .................................................. A61B 17/58
[52] U.S. Cl. .............................. 606/88; 606/102; 606/86; 606/96
[58] Field of Search ...................... 606/86, 87, 88, 606/89, 90, 96, 97, 98, 102, 105; 5/646, 647, 648, 649, 650, 651

[56] References Cited

U.S. PATENT DOCUMENTS

| Re. 34,762 | 10/1994 | Goble et al. | 606/96 |
|---|---|---|---|
| 4,407,277 | 10/1983 | Ellison | 5/650 |
| 4,467,801 | 8/1984 | Whiteside . | |
| 4,474,177 | 10/1984 | Whiteside . | |
| 4,524,766 | 6/1985 | Petersen . | |
| 4,571,834 | 2/1986 | Fraser et al. . | |
| 4,574,794 | 3/1986 | Cooke et al. | 606/88 |
| 4,773,407 | 9/1988 | Petersen . | |
| 4,807,618 | 2/1989 | Auchinleck et al. . | |
| 4,935,023 | 6/1990 | Whiteside et al. . | |
| 5,002,545 | 3/1991 | Whiteside et al. . | |
| 5,007,912 | 9/1991 | Albrektsson et al. . | |
| 5,104,103 | 4/1992 | Auchinleck et al. . | |
| 5,154,717 | 10/1992 | Matsen, III et al. . | |
| 5,201,325 | 4/1993 | McEwen et al. . | |
| 5,257,998 | 11/1993 | Ota et al. . | |
| 5,520,694 | 5/1996 | Dance et al. | 606/86 |

FOREIGN PATENT DOCUMENTS

| 1271102 | 7/1990 | Canada . |
|---|---|---|
| 326768A2 | 8/1989 | European Pat. Off. . |

*Primary Examiner*—Michael Powell Buiz
*Assistant Examiner*—Mark S. Leonardo
*Attorney, Agent, or Firm*—Arthur Jacob

[57] ABSTRACT

Method and apparatus for determining the direction of the mechanical axis of the femur of a patient in relation to the corresponding knee of the patient in connection with resecting the distal femur for the reception of a femoral knee prothesis include at least partially suspending the patient's leg to locate the knee at a suspended position wherein external forces on the knee, such as the weight of the leg, are balanced and the knee remains essentially stationary at the suspended position, applying a force to the femur at a predetermined location relative to the mechanical axis of the femur, directing the applied force in a direction such that the knee remains undeflected from the suspended position while the force is applied to the femur in that direction, and employing that direction of the applied force to indicate the direction of the mechanical axis of the femur.

14 Claims, 6 Drawing Sheets

METHOD AND APPARATUS FOR THE ALIGNMENT OF A FEMORAL KNEE PROSTHESIS

The present invention relates generally to method and apparatus for establishing the correct alignment and orientation for a femoral knee prosthesis during total knee arthroplasty surgery and pertains, more specifically, to determining the correct position and orientation of cutting guides with respect to a patient's femur so that the femur can be cut to fit the femoral knee prosthesis and the femoral knee prosthesis will be implanted in an anatomically correct orientation.

During knee resurfacing arthroplasty, commonly called knee replacement surgery, the distal surfaces of the femur are cut away and replaced with a metal cap to simulate the bearing surfaces of the femur. The proximal surface of the tibial is modified in a similar way, to provide a metal-backed plastic bearing surface. The metal femoral component of the new prosthetic joint transfers the weight of the patient to the tibial component such that the joint can support the patient's weight and provide a near-normal motion of the knee joint.

Several studies have indicated that the long term survival of a prosthetic knee joint is dependant on how accurately the components of the knee joint are implanted with respect to the weight bearing axis of the patient's leg. In a correctly functioning knee, the weight bearing axis passes through the center of the head of the femur, the center of the knee and the center of the ankle joint. This weight bearing axis typically is located by analyzing an X-ray image of the patient's leg, taken while the patient is standing.

The X-ray image is used to locate the center of the head of the femur and to calculate the position of the head relative to selected landmarks on the femur. The selected landmarks are then found on the patient's femur during surgery and the calculations used to estimate the actual position of the femoral head. These two pieces of information are used to determine the correct alignment of the weight bearing axis for the femur, commonly referred to as the mechanical axis of the femur. To completely define the correct position for the femoral component of the knee prosthesis, the correct relationship between the center of the femoral head and the knee joint and the rotation of the knee joint about the mechanical axis mast be established. This information is determined from landmarks on the distal portion of the femur. The correct alignment for the tibial component of the knee prosthesis is determined by finding the center of the ankle joint and relating its position to landmarks on the tibia. This point and the center of the proximal tibial plateau are used to define the weight bearing axis, or mechanical axis, of the tibia. The correct relationship between the ankle joint and the knee joint and the rotation of the knee joint about the mechanical axis are determined by reference to the dista portion of the femur and landmarks on the tibial plateau.

Various mechanical alignment instruments are used to assist the surgeon in making cuts on the distal femur and proximal tibia which will allow the femoral and tibial components of the prosthetic knee implant to be attached to the femur and tibia. These mechanical alignment instruments permit the surgeon to fix cutting guides in place with respect to the selected landmarks on the bones so that the cuts will be correctly oriented with respect to the mechanical axes determined from the X-ray image.

There are two general types of alignment instruments in common use. These are intramedullary and extramedullary alignment systems. Intramedullary alignment systems use the inside of the femur or tibia, the medullary canal, as one of the selected landmarks for establishing alignment. Extramedullary alignment systems use only the external surfaces of the body to establish alignment.

A typical extramedullary alignment system requires the surgeon to visually align a slender rod with the center of the knee and the center of the femoral head for alignment of the femoral component, then align a similar rod with the center of the ankle and the center of the tibial plateau for alignment of the tibial component. The centers of the femoral head and ankle are found by palpation or are established with an intraoperative X-ray. If correctly placed, the rods will lie parallel no, and offset from the mechanical axes. Once aligned, the rods are used as a guide to fix the location of the cutting guides with respect to the femur and the tibia so that the cuts can be performed.

A typical intramedullary alignment system requires the surgeon to insert rods into the medullary canal of the femur and of the tibia. If properly placed these rods should lie on the axis of the bones. In the case of the tibia, the mechanical axis is very close to the axis of the bone. In the case of the femur, the axis of the bone is quite different from the mechanical axis due to the offset nature of the hip joint, and this difference must be measured from the pre-operative X-ray and used to correct the alignment of the femoral cutting guides.

Both intramedullary and extramedullary approaches to alignment have numerous inherent drawbacks and sources of error. Extramedullary alignment depends on accurate visual estimation of the alignment of the extramedullary rods. Location of the femoral head by palpation is difficult and error-prone, particularly with obese patients. Use of intraoperative X-rays improves the result somewhat, but is time consuming and exposes the patient and operating room personnel to radiation. X-rays also are subject to distortion and require visual interpretation and estimation to analyze correctly, as X-rays offer only one planar view in two dimensions.

Intramedullary alignment approaches provide only sightly better results, in that the knee joint alignment is still determined by estimating the difference between the bone axis and the mechanical axis from a potentially distorted X-ray image. In addition, intramedullary rods must be introduced very carefully, not only to make sure they align correctly with the medullary canal, but also to make sure that the insertion of the rods does not create an embolism, which could seriously injure or even kill the patient.

An ideal alignment system finds the mechanical axis of the patient's leg directly, without the need for preoperative or intraoperative X-rays, estimation, calculation, location of hidden or obscured landmarks, or surgical intervention outside of that required for access to the knee joint surfaces. The ideal alignment system depends only on the accepted definition that the mechanical axis passes through the center of the head of the femur, the center of the knee joint and the center of the ankle, in order to locate the mechanical axis.

The present invention provides method and apparatus for locating the mechanical axis of a patient's femur by directly locating the center of rotation of the head of the femur. As such, the present invention attains several objects and advantages, some of which are summarized as follows: Enables accurate location of the direction of the mechanical axis of the femur interoperatively, without invading the medulliary canal and without the necessity for surgical intervention beyond that already required for access to the knee being replaced; provides a relatively simple procedure capable of being performed quickly just prior to preparing the femur for distal cuts; attains a high degree of accuracy with minimal procedural steps and apparatus; enables a direct determination of the direction of the mechanical axis of the femur without reliance upon visual estimation or interpretation; provides apparatus capable of long-term reliable performance.

The above objects and advantages, as well as further objects and advantages, are attained by the present invention which may be described briefly as method and apparatus for determining the direction of the mechanical axis of a femur of a patient in relation to the corresponding knee of the patient, the method comprising: the step of and means for placing the knee of the patient in an equilibrium position wherein external forces on the knee are balanced and the knee remains essentially stationary at the equilibrium position; the step of and means for applying a force to the femur at a predetermined location relative to the mechanical axis of the femur; the step of and means for directing the applied force in a direction such that the knee is undeflected from the equilibrium position while the force is applied to the femur in said direction; and the step of and means for employing said direction of the applied force to indicate the direction of the mechanical axis of the femur.

The invention will be understood more fully, while still further objects and advantages will become apparent, in the following detailed description of preferred embodiments of the invention illustrated in the accompanying drawing, in which.

Figure 1:
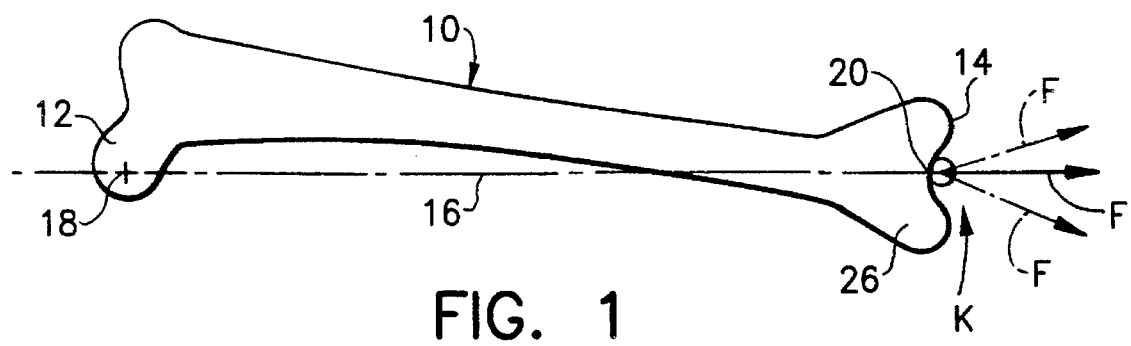
FIG. 1 is a schematic representation of the alignment method and system of the present invention.

Referring now to the drawing, and especially to FIG. 1 thereof, the femur of a supine patient is illustrated schematically at 10 and is seen to include a femoral head 12 and a distal end 14 at the knee K of the patient. The femur 10 is constrained for rotation about the femoral head 12 and the mechanical axis 16 of the femur 10 passes through the center of rotation 18 of the femoral head 12 and the center 20 of the knee K of the patient. It has been suggested that the location of the mechanical axis 16 can be determined by freely suspending the leg of the patient to permit free rotation of the femoral head 12 and then applying a tensile force at the center 20 of the knee to rotate the femur 10 until the mechanical axis 16 is aligned with the direction of the tensile force. Then, the direction of the tensile force serves as an indication of the location of the center of rotation 18 and the direction of the mechanical axis 16 relative to the center 20 of the knee, thereby locating the mechanical axis 16 and enabling that location to be used for the proper placement of cutting guides at the knee.

In practice, however, where a patient is supine on an operating table, the patient's leg cannot be fully freely suspended since the lower leg or the foot of the patient must remain on the operating table. As a result, a tensile force applied to the knee, as suggested above, must overcome external forces over and above the force necessary merely to rotate a freely suspended femur 10, thereby tending to introduce some deviation in the direction of the applied tensile force from the direction of the mechanical axis 16.

The present invention eliminates the effect of external forces in the determination of the direction of the mechanical axis 16 by eliminating the requirement for rotating the femur 10 in response to an applied tensile force and relying, rather, on the fact that the femur 10 will not rotate when a force is applied to the femur in a direction aligned with the mechanical axis 16 so as to pass through the center of rotation 18. Accordingly, in the method and apparatus of the present invention, the leg of the patient is partially suspended, at the knee K, so as to balance external forces at the knee and locate the knee at an equilibrium, or suspended, position. A force, illustrated in the form of a tensile force F, is applied to the distal femur 26, at the knee K, at a predetermined location relative to the mechanical axis 16. Force F is moved so as to be applied in directions parallel to the coronal plane, as illustrated in phantom as well as in full lines in FIG. 1, and any deviations in the location of the knee K from the suspended position, that is, any movements of the knee K within the coronal plane to either side of the suspended position while force F is applied to the knee, are observed until force F is oriented in a direction wherein the knee is undeflected from the suspended position and remains stationary at the suspended position. The direction of force F which produces no deflection of the knee from the suspended position, as illustrated in full lines in FIG. 1, is aligned parallel with the mechanical axis 16 and thus determines the direction of mechanical axis 16 in the coronal plane relative to the knee of the patient. The direction of the mechanical axis 16 in the sagittal plane is determined in a conventional manner, as will be explained in greater detail below. Once the direction of the mechanical axis 16 is fully determined, that direction is employed as a reference for the proper location of cutting guides used in the preparation of the distal femur 26 for the reception of a femoral knee prosthesis, as will now be described.

Figure 2:
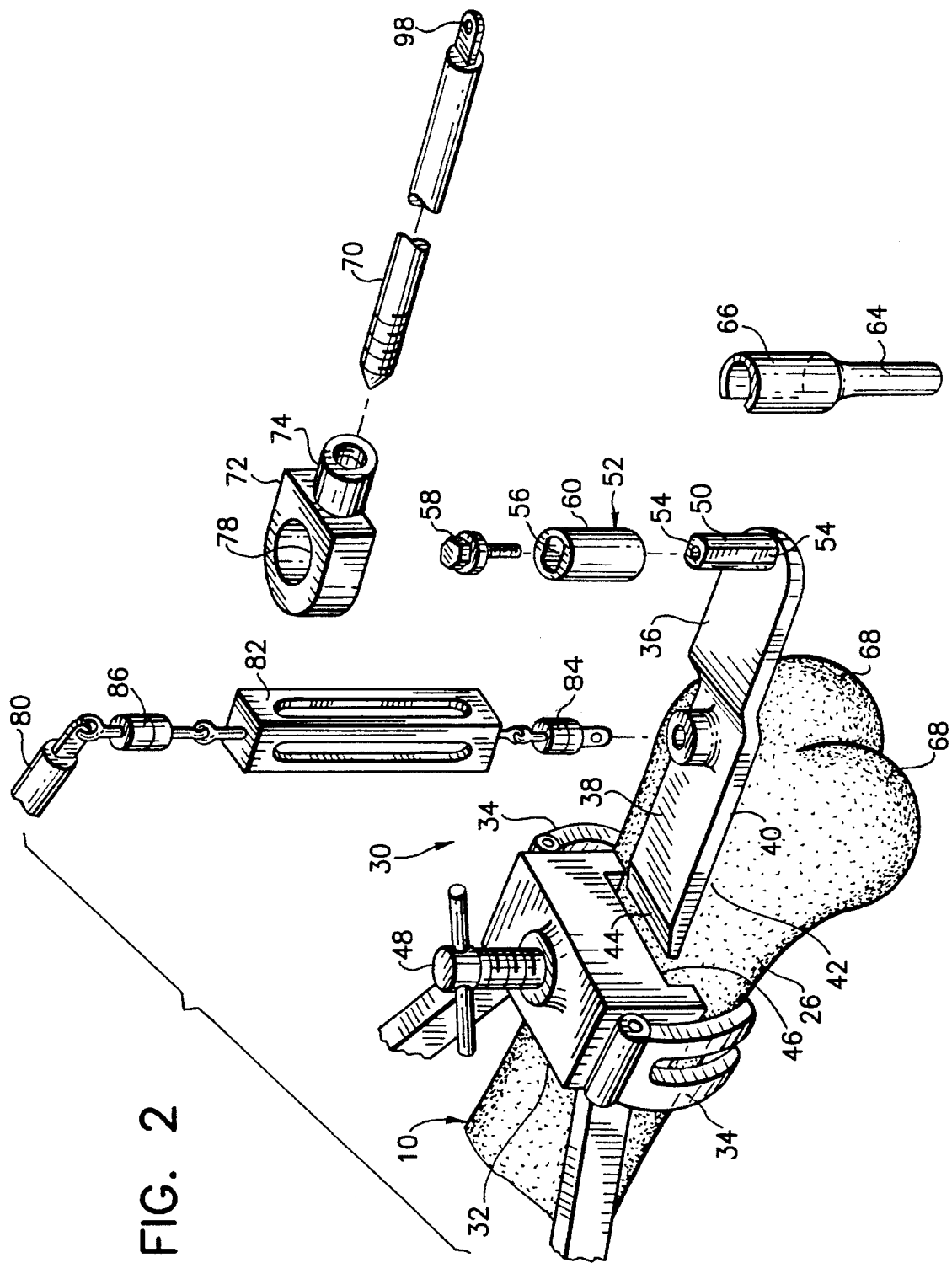
FIG. 2 is an exploded pictorial perspective view, partially schematic, of the alignment system of the present invention at the distal end of a femur.
Figure 3:
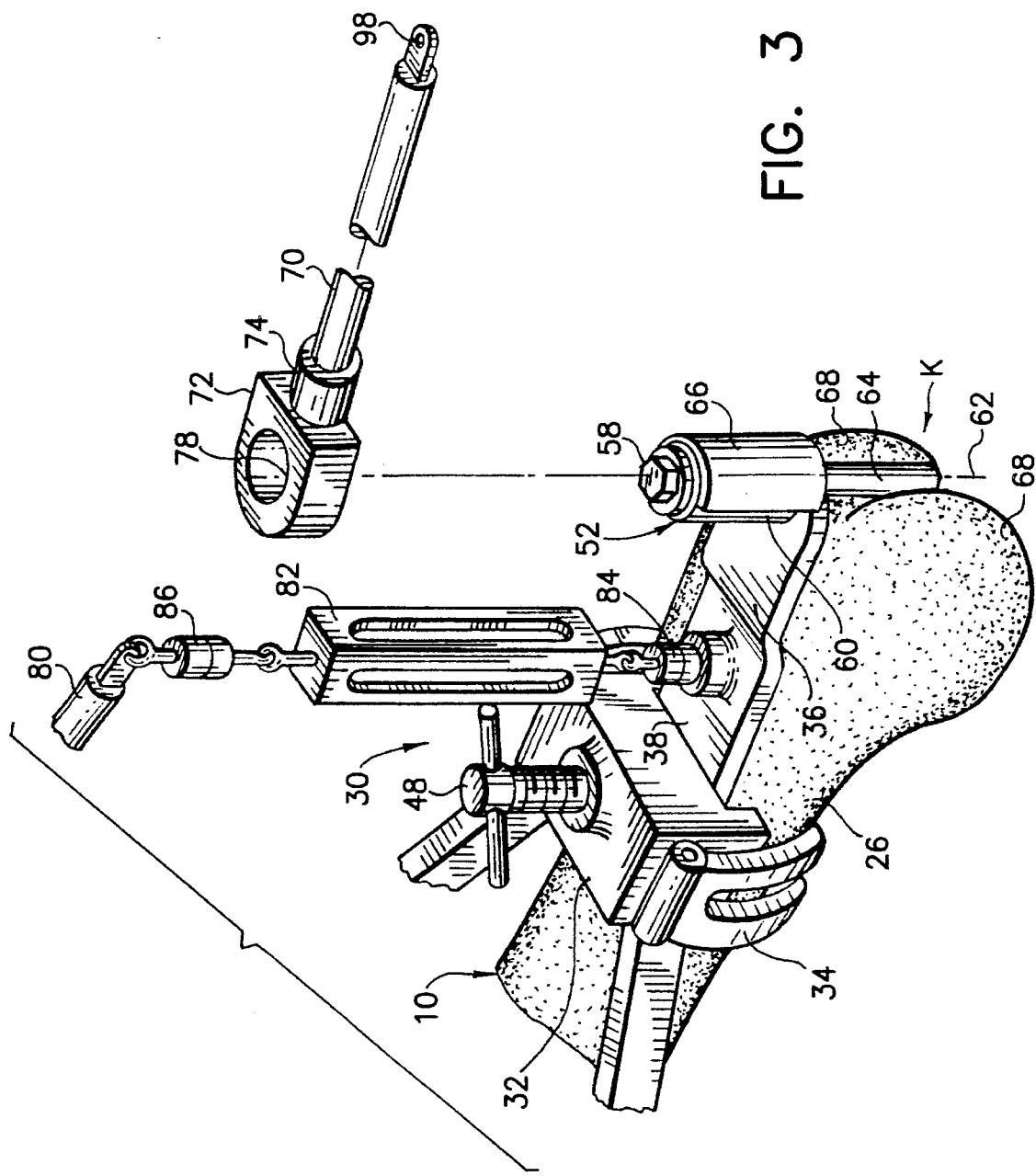
FIG. 3 is a pictorial perspective view, similar to FIG. 2, but only partially exploded.

Turning now to FIGS. 2 and 3, distal femur 26 is shown being prepared for the determination of the direction and location of the mechanical axis of the femur 10 and the subsequent implant of a femoral knee prosthesis not shown). Apparatus constructed in accordance with the present invention is illustrated generally at 30 and is seen to include securing means shown in the form of a femoral clamp 32 having clamping jaws 34 which grip the femur 10 to secure the femoral clamp 32 upon the exposed femur 10. An anterior reference member in the form of a bearing holder 36 includes an anterior reference bar 38 having an anterior reference surface 40 which is seated against the anterior cortex 42 of distal femur 26 when the anterior reference bar 38 is engaged with the femoral clamp 32, as seen in FIG. 3. Thus, anterior reference bar 38 includes a ramp 44 providing a wedge-shaped proximal end for facilitating insertion of the anterior reference bar 38 into a complementary channel 46 in the femoral clamp 32 and assuring direct contact between the anterior reference surface 40 and the anterior cortex 42. Femoral clamp 32 includes a clamping screw 48 which is tightened to clamp the anterior reference bar 38 in place, as seen in FIG. 3. Once clamped in place, with anterior reference surface 40 in intimate, fixed contact with anterior cortex 42, anterior reference bar 38 will be aligned with the sagittal component of the mechanical axis of femur 10.

A stud 50 is affixed at the distal end of the bearing holder 36 and projects in an anterior direction, normal to the coronal plane, to receive a bearing 52 placed over the stud 50 and secured to the stud 50 against rotation on the stud 50. To that end, stud 50 includes opposite flats 54 and bearing 52 includes a central opening 56 having a complementary configuration for securing the bearing 52 on the stud 50. A retainer screw 58 is affixed to the stud 50 to hold the bearing 52 in place on the stud 50 so that the bearing 52 provides a cylindrical bearing surface 60 extending in the anterior direction along an axis 62 normal to the coronal plane. An intercondylar post 64 includes a clip 66 which is snapped over the bearing 52 to secure the intercondylar post 64 to the bearing holder 36 with the intercondylar post 64 depending from the bearing holder 36, normal to the coronal plane, in the posterior direction.

Figure 4:
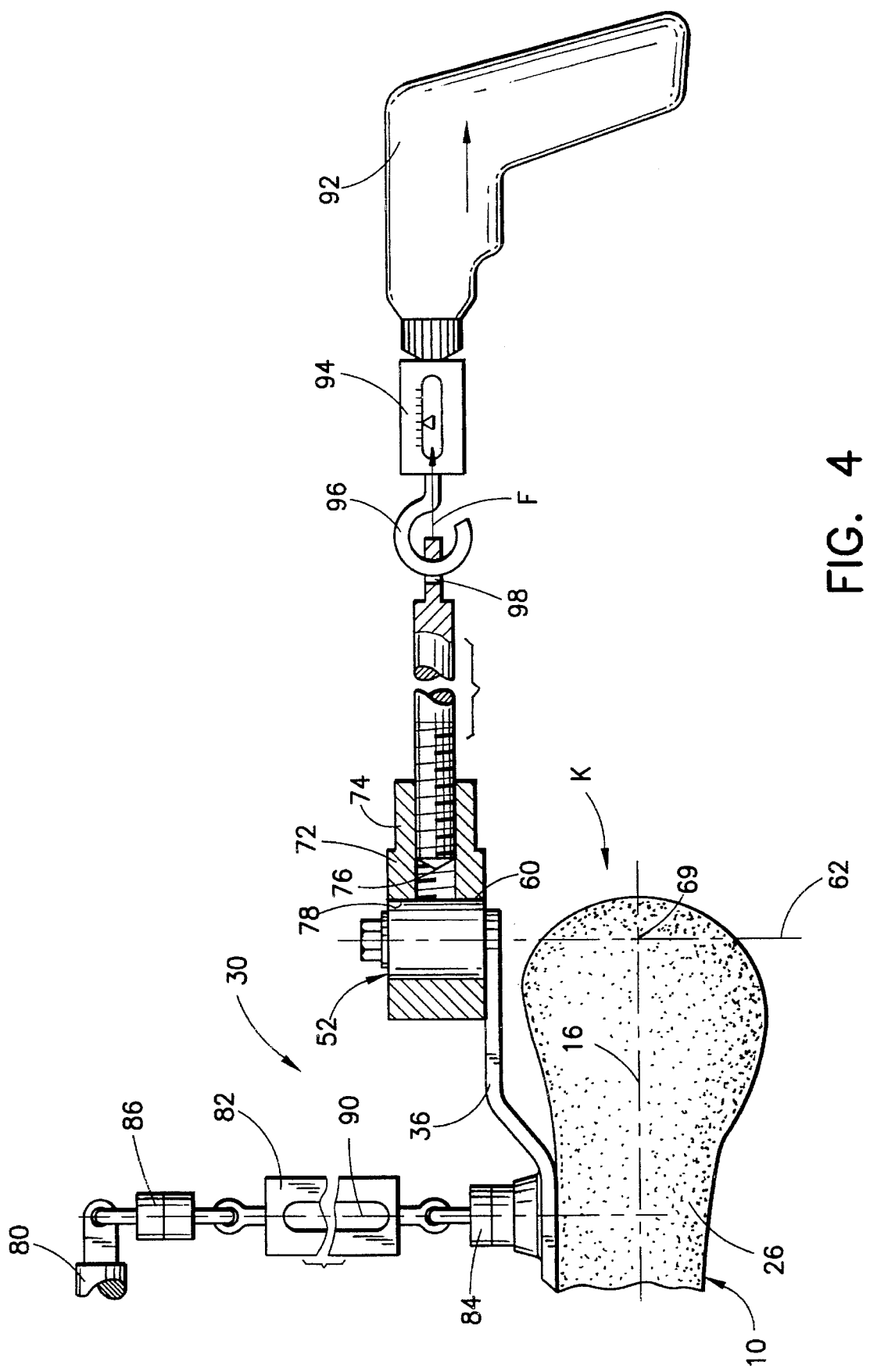
FIGS. 4 and 5 are enlarged fragmentary side elevational views, partially in cross-section, of a portion of the alignment system illustrating the method of the present invention.

Prior to clamping the bearing holder 36 in place, as seen in FIG. 3, bearing 52 is secured on stud 50 and intercondylar post 64 is clipped to bearing 52. Then, the proximal end of the anterior reference bar 38 is engaged with the femoral clamp 32, with the intercondylar post 64 assisting in the proper positioning of the bearing holder 36, by virtue of the placement of the intercondylar post 64 between the condyles 68 of the distal femur 26 and perpendicular to the coronal plane. Once the bearing holder 36 is clamped in place, as seen in FIG. 3, the intercondylar post 64 is removed from the bearing 52, and the cylindrical bearing surface 60 of the bearing 52 is exposed, extending along axis 62 normal to the coronal plane and intersecting the mechanical axis 16, as illustrated at 69 in FIG. 4. As seen in FIG. 4, as well as in FIG. 3, an alignment member in the form of an elongate alignment rod 70 is coupled with a collar 72 by means of a threaded coupling 74 and includes a pointed tip 76 which initially is recessed with respect to a bore 78 in the collar 72. Bore 78 is complementary to the cylindrical bearing surface 60 of bearing 52 so that alignment rod 70 can be coupled with bearing 52 by slipping collar 72 over bearing 52, with collar 72 journaled for rotation on bearing 52, to enable pivotal movement of the alignment rod 70 about axis 62.

The leg of the patient is partially suspended by connecting the bearing holder 36 to a support arm 80 located above the femur 10, as seen in FIGS. 3 and 4. A vertical alignment and suspension device, shown somewhat schematically at 82, is connected between the bearing holder 36 and the support arm 80, as by suspension couplings 84 and 86. Support arm 80 is a part of a positioning system which may be manipulated by the surgeon to swing the support arm 80 directly over the femur 10 so as to facilitate attachment of the vertical alignment and suspension device 82 at couplings 84 and 86, and suspension of the patient's leg. Then the patient's leg is elevated until the weight of the leg is substantially supported by the support arm 80. Once the patient's leg is suspended, with the weight of the leg largely supported by the support arm 80, the position of the support ark 80 is fixed and the patient's knee K is placed in the suspended position illustrated in FIG. 4, in which suspended position the vertical alignment and suspension device 82 indicates that the line of suspension 90 is truly vertical with respect to gravity. In this equilibrium position of the knee, all external forces on the knee are balanced, and the knee remains essentially stationary. One positioning system currently available for use in positioning support arm 80 is known as the ENDEX endoscopy positioning system sold by Andronic Devices Ltd. of Richmond, B.C., Canada. Vertical alignment and suspension device 82 may be in the form of a simple mechanical plumb bob arrangement which provides a visual indication of plumb, that is, vertical alignment along the line of suspension 90, or may be in the form of an electronic plumb indicator.

Figure 5:
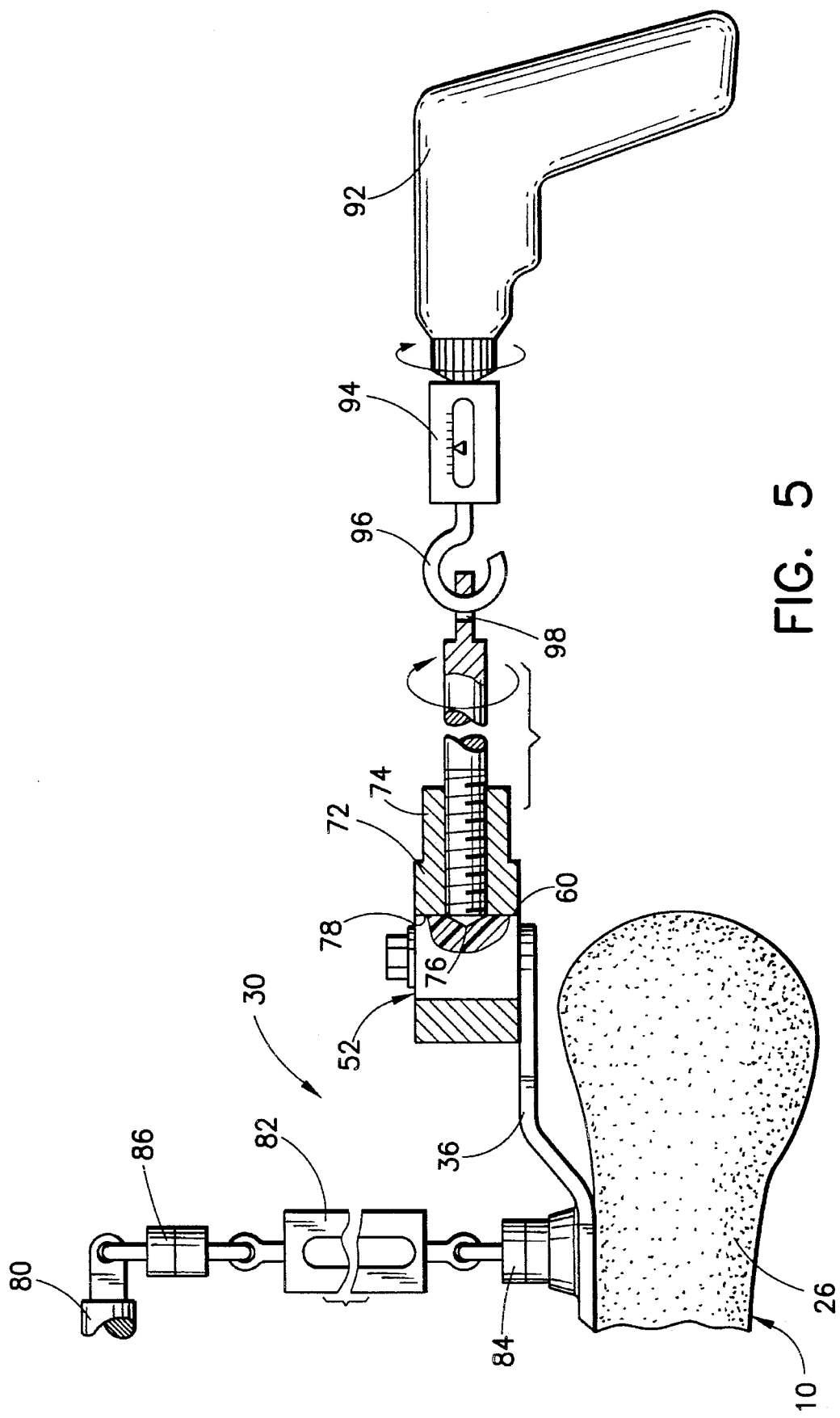

As best seen in FIGS. 4 and 5, a powered surgical drill 92 subsequently is coupled to the distal end of the alignment rod 70, through a force indicator 94, by means of a coupling arrangement shown in the form of a hook 96, affixed to the surgical drill 92 for rotation by the surgical drill 92, and passed through an eye 98 at the distal end of alignment rod 70. The surgeon then pulls upon the surgical drill 92, in the direction illustrated, to apply a force along the alignment rod 70, which force is transmitted to the bearing 52 and the bearing holder 36, and observes the force indicator 94 to gage the amount of force exerted. Preferably, a tensile force of at least about ten pounds is applied to alignment rod 70 to establish force F. Force F thus is applied to the femur 10 at the predetermined location established by the location and orientation of bearing 52 by means of the surgical drill 92 coupled to the knee K through the alignment rod 70, the force indicator 94, the hook 96 and the eye 98, and pulled upon by the surgeon to establish the tensile force. As force F is applied to the alignment rod 70, the angular direction of the force F is changed by the surgeon, in directions parallel to the coronal plane, by angular pivotal movement of the alignment rod 70 about axis 62, with collar 72 journaled on bearing surface 60 of bearing 52 serving as means for directing the applied force F, to align force F so that the knee K is maintained stationary at the suspended position, and is undeflected from the suspended position, as observed by indications provided by the vertical alignment and suspension device 82, while force F is applied to the femur 10 at the knee K.

Upon reaching the angular position of alignment rod 70 where the knee K remains undeflected from the suspension position while force F is applied to the knee K, the alignment rod 70 is locked in place by actuating the powered surgical drill 92 to rotate alignment rod 70 about the longitudinal axis of the alignment rod 70, as indicated by the arrow in FIG. 5. Such rotation of the alignment rod 70 advances the pointed tip 76 of the alignment rod 70, by means of the thread ed coupling 74, to embed the pointed tip 76 in the bearing 52, as seen in FIG. 5, and secure the angular position of the alignment rod 70 relative to the fixed bearing 52 the pointed tip 76 of the alignment rod 70 and the bearing 52 thus serving as means for employing the direction of the applied force F to indicate the direction of the mechanical axis of the femur 10. The coupling arrangement provided by the hook 96 and eye 98 assures that both the force along alignment rod 70 required to establish force F and the torque required to rotate alignment rod 70 to lock the alignment rod 70 in place are applied without a moment which would tend to displace the alignment rod 70 from the proper angular position. Bearing 52 preferably is constructed of a synthetic polymeric material having sufficient lubricity to facilitate the necessary angular movements of the alignment rod 70, as described above, while enabling a fixed connection through the use of pointed tip 76. Once used, the bearing 52 is discarded and replaced by a new bearing 52; hence, the material of the bearing 52 should render the bearing 52 economically expendable.

Figure 6:
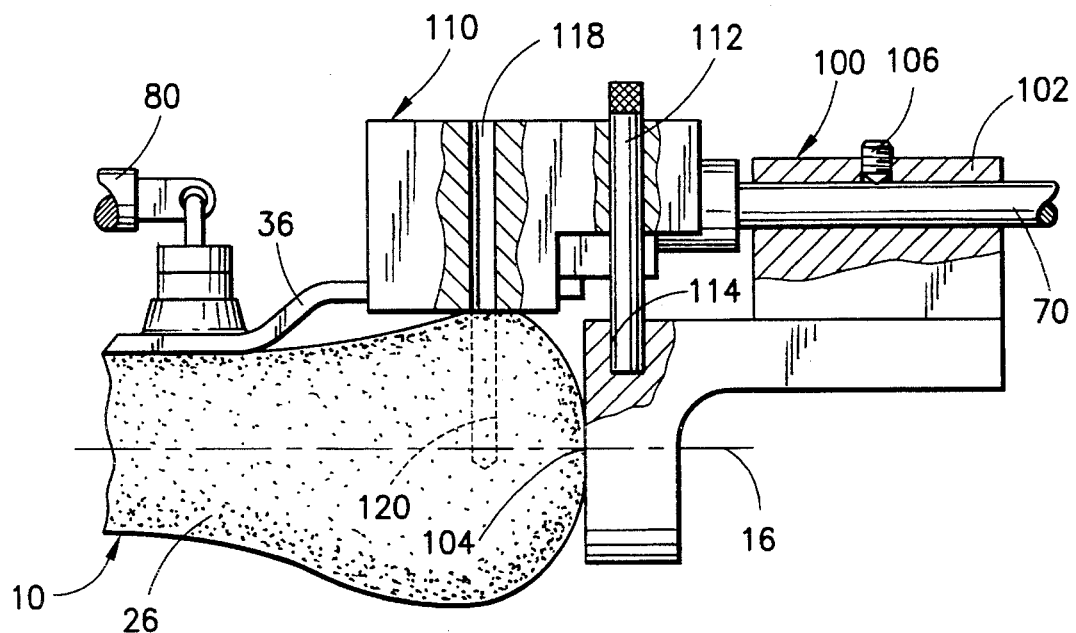
FIG. 6 is an enlarged fragmentary side elevational view similar to FIGS. 4 and 5, but showing the location of guides at the distal end of the femur.

With the alignment rod 70 affixed on the bearing 52, as described above, the direction in which the alignment rod 70 extends is parallel with the mechanical axis 16 of femur 10 and the direction of the mechanical axis 16 is determined. Further, since alignment rod 70 is parallel with the mechanical axis 16, alignment rod 70 now is available for use in locating cutting guides for making the cuts necessary to prepare the distal femur 26 for the reception of the femoral knee prosthesis to be implanted. Turning now to FIG. 6, the surgical drill 92 and the force indicator 94 are removed from the alignment rod 70, the vertical alignment and suspension device 82 is uncoupled from the bearing holder 36 and the support arm 80, and the support arm 80 is affixed directly to the bearing holder 36 so that the femur 10 is held in place, essentially rigidly, by the support arm 80.

The alignment rod 70 now is available to receive a distal femoral condyle locator 100 which is slipped over the distal end of the alignment rod 70 and translated along the alignment rod 70 until the femoral condyle locator 100 engages the distal end of the femur 10. The femoral condyle locator 100 includes a sleeve 102 for sliding along the alignment rod 70 and a locator surface 104 which is maintained perpendicular to alignment rod 70 by the engagement of the sleeve 102 with the alignment rod 70. Once in place, as illustrated in FIG. 6, femoral condyle locator 100 is secured in place by a set screw 106. A femoral drill guide 110 then is mounted upon the femoral condyle locator 100 by engaging pins 112 through the femoral drill guide 110 and into corresponding holes 114 in the femoral condyle locator 100 to lock the femoral drill guide 110 in place. Femoral drill guide 110 includes a plurality of drill alignment holes 118, any matched pair of which may be selected by the surgeon for drilling corresponding locator holes 120 in the femur 10. Thus, locator holes 120 are placed in appropriate position relative to the mechanical axis 16 of the femur 10 for the reception of standard cutting guides for the resection of the distal femur 26. Apparatus 30 is removed from distal femur 26 by removing the femoral drill guide 110 from the femoral condyle locator 100, then removing the femoral condyle locator 100 from the alignment rod 70, then uncoupling the alignment rod 70 from the bearing 52, uncoupling the support arm 80 from the bearing holder 36, loosening the clamping screw 48 to detach the bearing holder 36 from the femoral clamp 32 and then removing the femoral clamp 32 from the femur 10. Locator holes 120 are then available for use in connection with conventional cutting guides.

Figure 7:
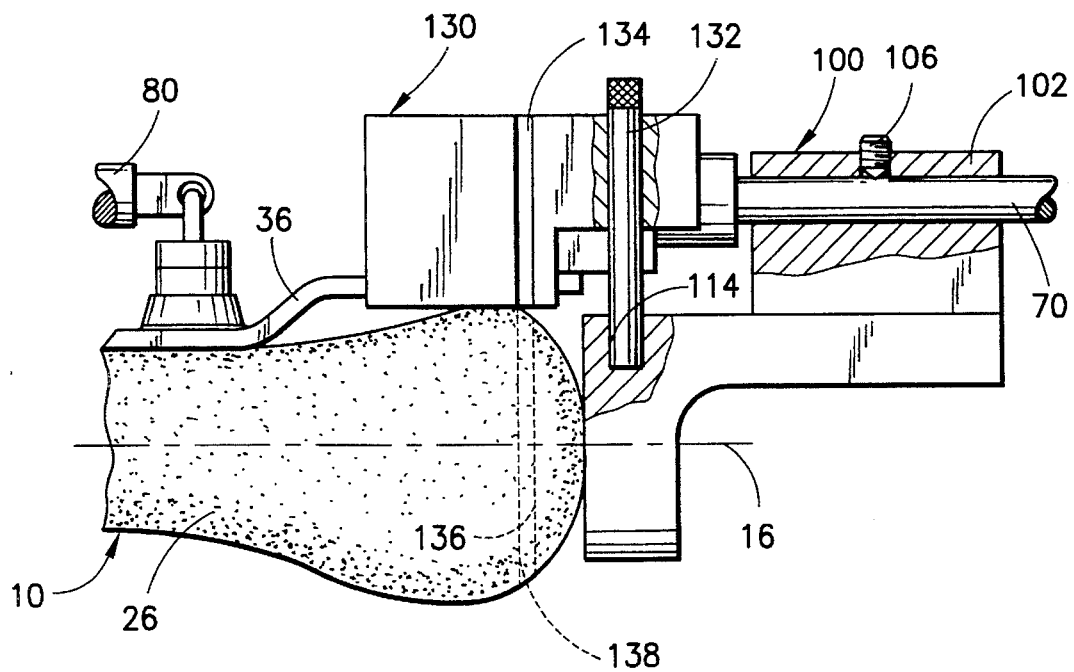
FIG. 7 is a side elevational view similar to FIG. 6, with an alternate guide.

In an alternate arrangement illustrated in FIG. 7, rather than locating the femoral drill guide 110 on the femoral condyle locator 100, a distal femoral resection guide 130 is located on the femoral condyle locator 100, as by pins 132 extending through the femoral resection guide 130 to enter a corresponding selected set of holes 114 in the femoral condyle locator 100. The distal femoral resection guide 130 then is locked to the alignment rod 70, by virtue of pins 132 engage d with holes 114 in the femoral condyle locator 110 which is secured in place by set screw 106. Slots 134 are provided in the distal femoral resection guide 130 in position to guide a cutting instrument, such as a saw, for executing distal femoral cuts 136. Apparatus 30 then is removed from the femur 10, as described above, and resection of the distal femur 26 is completed in a conventional manner, utilizing the distal femoral surfaces 138 established by femoral cuts 136.

It will be seen that the present invention attains the several objects and advantages summarized above, namely: Enables accurate location of the direction of the mechanical axis of the femur interoperatively, without invading the medullary canal and without the necessity for surgical intervention beyond that already required for access to the knee being replaced; provides a relatively simple procedure capable of being performed quickly just prior to preparing the femur for distal cuts; attains a high degree of accuracy with minimal procedural steps and apparatus; enables a direct determination of the direction of the mechanical axis of the femur without reliance upon visual estimation or interpretation; provides apparatus capable of long-term reliable performance.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for determining the direction of the mechanical axis of a femur of a patient in relation to the corresponding knee of the patient, the apparatus comprising:

means for placing the knee of the patient in an equilibrium position wherein external forces on the knee are balanced so that the knee remains essentially stationary at the equilibrium position and is freely deflectable from the equilibrium position in response to a further external force applied to the femur;

means for applying a force to the femur at a predetermined location relative to the mechanical axis of the femur;

means for directing the applied force in a direction such that the knee is undeflected from the equilibrium position while the force is applied to the femur in said direction; and means for employing said direction of the applied force to indicate the direction of the mechanical axis of the femur.

2. The apparatus of claim 1 wherein the means for applying a force to the knee includes means for applying a tensile force.

3. The apparatus of claim 1 including means for locating a cutting guide on the femur so aligned with said direction as to enable the cutting guide to be located in appropriate relation to the mechanical axis of the femur.

4. The apparatus of claim 1 wherein the means for placing the knee of the patient in the equilibrium position includes means for at least partially suspending the corresponding leg of the patient at the knee such that the equilibrium position of the knee is a suspended position.

5. The apparatus of claim 4 wherein the means for applying a force to the knee includes means for applying a tensile force.

6. Apparatus for locating the mechanical axis of a femur, in the coronal plane, of a supine patient in relation to the corresponding knee of the patient, the apparatus comprising:

means for at least partially suspending the corresponding leg of the patient at the knee such that the knee is located at a suspended position wherein external forces on the knee are balanced and the knee remains essentially stationary at the suspended position;

means for applying a force to the femur at a predetermined location relative to the mechanical axis of the femur;

means for directing the applied force in a direction in the coronal plane such that the knee is undeflected from the suspended position while the force is applied to the femur in said direction; and means for employing said direction of the applied force to indicate the location of the mechanical axis of the femur, in the coronal plane.

7. The apparatus of claim 6 wherein the predetermined location is on an axis normal to the coronal plane and intersecting the mechanical axis of the femur.

8. The apparatus of claim 6 wherein the means for applying a force to the knee includes means for applying a tensile force.

9. The apparatus of claim 6 including means for locating a cutting guide on the femur in accordance with said direction so as to enable the cutting guide to be located in appropriate relation to the mechanical axis of the femur.

10. Apparatus for locating the mechanical axis of a femur, in the coronal plane, of a supine patient in relation to the corresponding knee of the patient, interoperatively, in connection with the implant of a femoral knee prosthesis, the apparatus comprising:

an anterior reference member;

securing means for securing the anterior reference member at the anterior cortex of the femur;

suspension means adapted to be coupled to the anterior reference member for suspending the corresponding leg of the patient at the knee such that the knee is located at a suspended position wherein external forces on the knee are balanced and the knee remains essentially stationary at the suspended position;

indicator means couple with the suspension means for indicating when the knee is at the suspended position;

pivot means on the anterior reference member, the pivot means providing a pivotal axis for intersecting the mechanical axis of the femur when the anterior reference member is secured at the anterior cortex of the femur, with the pivotal axis extending normal to the coronal plane;

an alignment member;

pivot coupling means for coupling the alignment member with the pivot means for pivotal movement of the alignment member about the pivotal axis;

force applying means adapted to be coupled to the femur for applying a force to the femur in a direction along the alignment member, when the alignment member is coupled with the pivot means, such that pivotal movement of the alignment member enables selection of the direction of the force applied to the femur, along the alignment member, in the coronal plane;

the pivot means including locking means for locking the alignment member against further pivotal movement when the direction of the applied force is selected such that the indicator means indicates that the knee is in the suspended position while the force is applied to the femur in the selected direction, whereby the alignment member is aligned and secured parallel with the mechanical axis of the femur.

11. The apparatus of claim 10 wherein the force applying means is coupled to the alignment member.

12. The apparatus of claim 10 including a femoral guide, the alignment member comprising an alignment rod adapted to project from the femur for the reception of the femoral guide to be located on the femur so aligned with the direction in which the alignment rod projects as to enable the femoral guide to be located in appropriate relation to the mechanical axis of the femur.

13. The apparatus of claim 12 wherein the force applying means is coupled to the alignment rod.

14. The apparatus of claim 13 wherein the force applying means is coupled with the alignment rod for the application of a tensile force to the alignment rod.

* * * * *